US009942452B2

(12) United States Patent
Wei et al.

(10) Patent No.: US 9,942,452 B2
(45) Date of Patent: Apr. 10, 2018

(54) OPTOELECTRONIC MODULE AND AN IMAGING APPARATUS COMPRISING THE SAME

(71) Applicant: NINGBO WISE OptoMech Technology Corporation, Ningbo (CN)

(72) Inventors: Xibo Wei, Ningbo (CN); Geping Liu, San Jose, CA (US); Jingjing Wei, Ningbo (CN)

(73) Assignee: Ningbo WISE OptoMech Technology Corporation, City of Ningbo, Zhejiang Province (CN)

( * ) Notice: Subject to any disclaimer, the term of this patent is extended or adjusted under 35 U.S.C. 154(b) by 0 days.

(21) Appl. No.: 15/246,636

(22) Filed: Aug. 25, 2016

(65) Prior Publication Data

US 2018/0063387 A1 Mar. 1, 2018

(51) Int. Cl.
*A61B 1/04* (2006.01)
*H04N 5/225* (2006.01)
*A61B 1/00* (2006.01)
*A61B 1/06* (2006.01)
*A61B 1/005* (2006.01)
*G02B 23/24* (2006.01)

(52) U.S. Cl.
CPC ....... *H04N 5/2253* (2013.01); *A61B 1/00016* (2013.01); *A61B 1/00034* (2013.01); *A61B 1/00039* (2013.01); *A61B 1/0052* (2013.01); *A61B 1/00165* (2013.01); *A61B 1/0684* (2013.01); *G02B 23/2484* (2013.01); *H04N 5/2254* (2013.01); *H04N 5/2256* (2013.01)

(58) Field of Classification Search
CPC .. H04N 5/2253; H04N 5/2254; H04N 5/2256; A61B 1/00016; A61B 1/00034; A61B 1/00039; A61B 1/00165; A61B 1/0052; A61B 1/0684; G02B 23/2484

USPC .......................................................... 348/68
See application file for complete search history.

(56) References Cited

U.S. PATENT DOCUMENTS

| | | | |
|---|---|---|---|
| 7,022,066 B2 * | 4/2006 | Yokoi | A61B 1/04 348/65 |
| 7,668,450 B2 | 2/2010 | Todd et al. | |
| 8,092,376 B2 | 1/2012 | Suda | |
| 8,928,746 B1 | 1/2015 | Stevrin et al. | |
| 2001/0017649 A1 * | 8/2001 | Yaron | A61B 1/00193 348/45 |
| 2005/0085690 A1 * | 4/2005 | Tien | A61B 1/00105 600/109 |
| 2011/0092892 A1 * | 4/2011 | Nitsan | A61B 1/00068 604/28 |
| 2013/0221848 A1 | 8/2013 | Miesak | |

(Continued)

*Primary Examiner* — Christopher S Kelley
*Assistant Examiner* — Matthew Kwan
(74) *Attorney, Agent, or Firm* — Guosheng Wang; United States Research and Patent Firm

(57) ABSTRACT

The present invention provides an optoelectronic module and an imaging apparatus such as an endoscope comprising such module. The optoelectronic module includes a housing and an image sensor. The image sensor's face has a perimeter S, the cross section of the optoelectronic module along the face has a perimeter H, and S<H<1.6S. In an example, illumination components such as a flashing LED and the image sensor are confined within the minimum bounding circle of the sensor's face. The invention exhibits technical advantage in minimizing the size of the insert portion of the endoscopy.

18 Claims, 13 Drawing Sheets

(56) References Cited

U.S. PATENT DOCUMENTS

| | | | |
|---|---|---|---|
| 2014/0225998 A1* | 8/2014 | Dai | H01L 27/14601 348/65 |
| 2014/0320617 A1* | 10/2014 | Parks | A61B 1/00181 348/65 |
| 2015/0062299 A1* | 3/2015 | Brown | H04N 13/0239 348/45 |
| 2017/0064162 A1* | 3/2017 | Haraguchi | H04N 5/2252 |

* cited by examiner

OPTOELECTRONIC MODULE AND AN IMAGING APPARATUS COMPRISING THE SAME

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention generally relates to an optoelectronic module and an imaging apparatus such as a medical or industrial endoscope using such optoelectronic module. More particularly, the present invention is related to a small optoelectronic module including an image sensor, an illumination component, and other optional component(s).

BACKGROUND OF THE INVENTION

Endoscopes of small size are desired in many industrial and medical applications. For example, when natural orifices and lumens of a human body are small, small endoscopes are required for insertion through such orifices and lumens to target locations within the body. For single incision laparoscopy, smaller endoscopes are preferred to provide an inside-the-body view of the surgical site, particularly when the incision itself is of minimal dimensions. Sometimes, patients may feel irritating when an endoscope is being inserted into his or her body, and a smaller endoscope may mitigate such unpleasant experience and may minimize trauma to the patient. Moreover, a physician may improve diagnostic and procedural protocols with a smaller endoscope. For example, transnasal endoscopy may sometimes replace trans-oral endoscopy.

To meet the small-size requirement, an apparent solution is to decrease the size of each individual component within the endoscope, for example, using a smaller size camera or a smaller size fiber bundle. However, there are limits to how much reduction can be achieved, and each size reduction has its cost in terms of performance and assembly complexity. Advantageously, the present invention provides a new solution to solve the problems.

SUMMARY OF THE INVENTION

One aspect of the present invention provides an optoelectronic module comprising a housing and an image sensor. The image sensor is located within the housing, and it has a face (e.g. a non-circular face) with a perimeter S. The cross section of the optoelectronic module along the face has a perimeter H. In various embodiments, S<H<1.6S.

Another aspect of the invention provides an imaging apparatus for imaging the interior surface of a tubular structure. The apparatus includes (1) the optoelectronic module as described above for insertion into the tubular structure; (2) a receiving device outside the tubular structure for receiving the signal from the image sensor; and (3) a cable having (i) a distal end connected to the proximal end of the optoelectronic module, and (ii) a proximal end connected to the receiving device.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form in order to avoid unnecessarily obscuring the present invention. Other parts may be omitted or merely suggested.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

Figure 1:
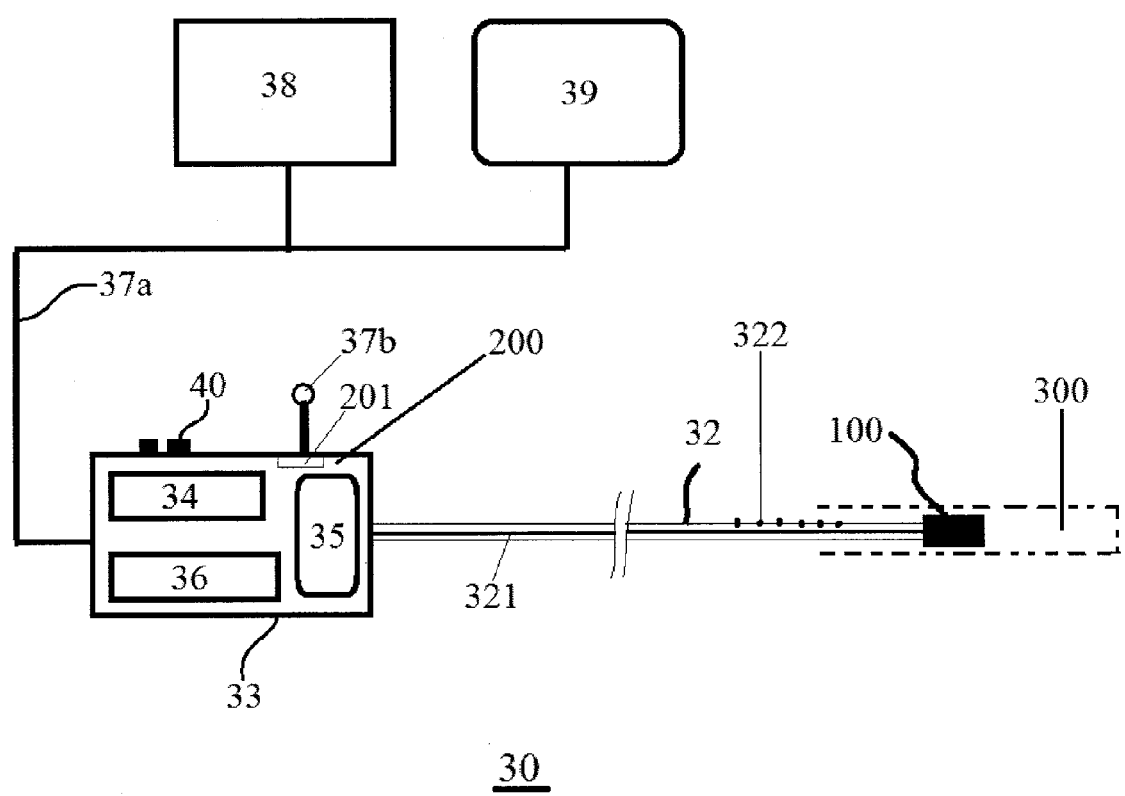
FIG. 1 illustrates an endoscope as one example of the imaging apparatus in accordance with an exemplary embodiment of the present invention.

As illustrated in FIG. 1, an exemplary embodiment of the imaging apparatus for imaging the interior surface of a tubular structure 300 is shown as endoscope 30. When tubular structure 300 is, for example, a lumen in the body of human or animal, endoscope 30 becomes an instrument useful for human medicine and veterinary medicine. However, it should be appreciated that endoscope 30 may be employed as an industrial endoscope, when tubular structure 300 is a part of an industrial apparatus, an equipment, a product, a machine, a production line, and the like.

Endoscope 30 includes an optoelectronic module 100 with a shell-like housing configured for insertion into tubular structure 300 for imaging its interior surface. For example, optoelectronic module 100 may be inserted into a patient's body through a natural body orifice, such as the mouth, nose, urethra, bladder, vagina, or anus. Endoscope 30 can therefore have different configurations for using as a gastroscope, a colonoscope, endoscopic ultrasound (EUS), endoscopic retrograde cholangiopancreatography (ERCP), or the like. Applications of endoscope 30 include diagnostic observation associated with endomaterial polyps, infertility, abnormal bleeding, and pelvic pain; and surgical procedure such as embryo growth arrest and uterine malformation etc.

Endoscope 30 may further include a tube or cable 32 having (i) a distal end connected to the proximal end of optoelectronic module 100, and (ii) a proximal end connected to receiving device 200. Cable 32 may be flexible, rigid, or semi-rigid, and is configured to extend proximately through the tubular structure 300 to enable a force to be applied to optoelectronic module 100 to control the movement thereof within tubular structure 300, and to permit retraction of optoelectronic module 100 from tubular structure 300.

Receiving device 200 is generally located outside tubular structure 300 for receiving the signal from an image sensor (as will be described later) within optoelectronic module 100. For example, cable 32 may include at least one electrical lead 321 that is coupled to optoelectronic module 100 and conveys an electrical signal from optoelectronic module 100 to receiving device 200. Cable 32 may be detachably coupled to (or removably connected to) housing 33 of receiving device 200, which may contain, for example, processor board 34, camera board and frame grabber 35 and power source 36. The power source 36 may be, for example, one or more conventional dry-cell disposable batteries or lithium ion rechargeable batteries. Processor board 34 may be coupled by cable 37a to computer 38 for storage and retrieval of images generated by endoscope 30. Alternatively or in addition, housing 33 may include antenna 37b and a wireless chipset 201, e.g., compliant with the IEEE 802.11 WiFi standards, for wirelessly transmitting the video image generated by endoscope 30 to computer 38 or display 39 without cable 37a. This arrangement may be particularly preferred for use in a physician's office because it permits the computer and display to be placed outside of the sterile field, while also allowing the physician greater maneuverability during use of endoscope 30.

Alternatively or in addition, computer 38 may be programmed with image processing software that takes as input the image data output from endoscope 30 and generates two- or three-dimensional reconstructions of the body lumen that may be displayed on display 39. A display that can display a moving image (movie), and is implemented by a CRT, a liquid crystal monitor, or the like.

In exemplary embodiments, a processor programmed with software may accept as input a plurality of still images of an object generated by the optoelectronic module 100 and output for display a three-dimensional rendering of the object based on the plurality of still images. Housing 33 may also include switches 40 for activating optoelectronic module 100, for switching image mode, and for activating frame grabber 35 to create a still image from the video stream output generated by optoelectronic module 100.

Cable 32 may be configured to couple optoelectronic module 100 to the circuitry within housing 33 in any suitable manner. For example, the availability of low-cost modular imaging system components enables the manufacture of a disposable components of the endoscope 30 at very low cost. In one embodiment, cable 32 is configured to detachably couple optoelectronic module 100 to the circuitry within housing 33. In this manner, cable 32 and optoelectronic module 100 are disposable, and may be detached from housing 33 after a single patient use, thus eliminating the need for sterilization or reprocessing and reducing contamination risks. Housing 33 may be disinfected for subsequent reuse with a new cable and optoelectronic module for a different patient.

In preferred embodiments, cable 32 may serve as a tether, and may include a plurality of scale markings or fiducials 322 that enable a physician to measure a distance traveled by optoelectronic module 100 into tubular structure 300 such as a lumen of a body.

Other known structure(s) may be built into endoscope 30 as desired. For example, an ergonomic handle can be used for easy operation. A mechanism can be introduced in the endoscope to curve cable 32. The physician may bend or curve the cable by pulling or loosening a wire (not shown). Module 100 may be turned or maneuvered by way of a flexible shaft or cable 32.

Endoscope 30 may be operated to perform or complete selected tasks manually, automatically, or a combination thereof. Some endoscopic functions may be implemented with the use of components that comprise hardware, software, firmware or combinations thereof. While general-purpose components such as general purpose computers or oscilloscopes can be used in endoscope 30, dedicated or custom components such as circuits, integrated circuits or software can be too. For example, some functions are implemented with a plurality of software instructions executed by a data processor, which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more input devices (e.g., allowing input of commands and/or parameters) and output devices (e.g., allowing reporting parameters of operation and results).

Figure 2A:
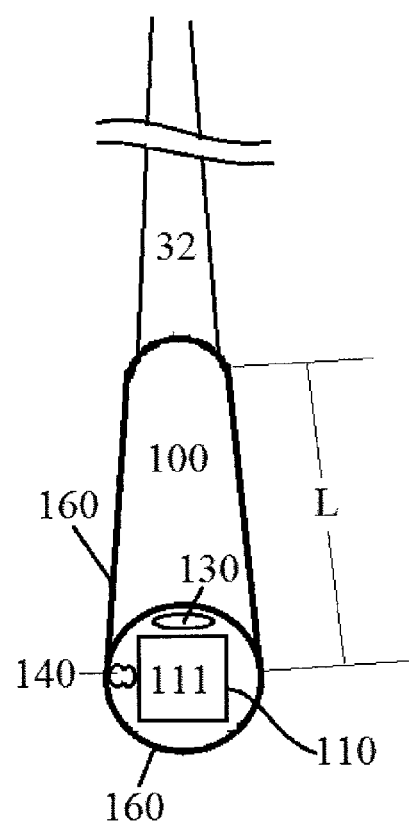
FIG. 2A schematically demonstrates a general optoelectronic module in accordance with an exemplary embodiment of the present invention.
Figure 2B:
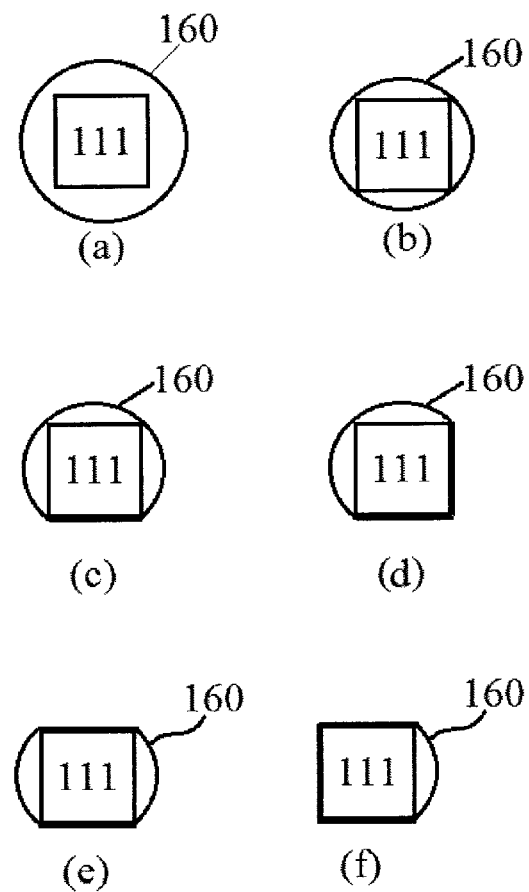
FIG. 2B is the cross-sectional view of various optoelectronic module having different designs of the image sensor's face and the housing in accordance with an exemplary embodiment of the present invention.
Figure 3A:
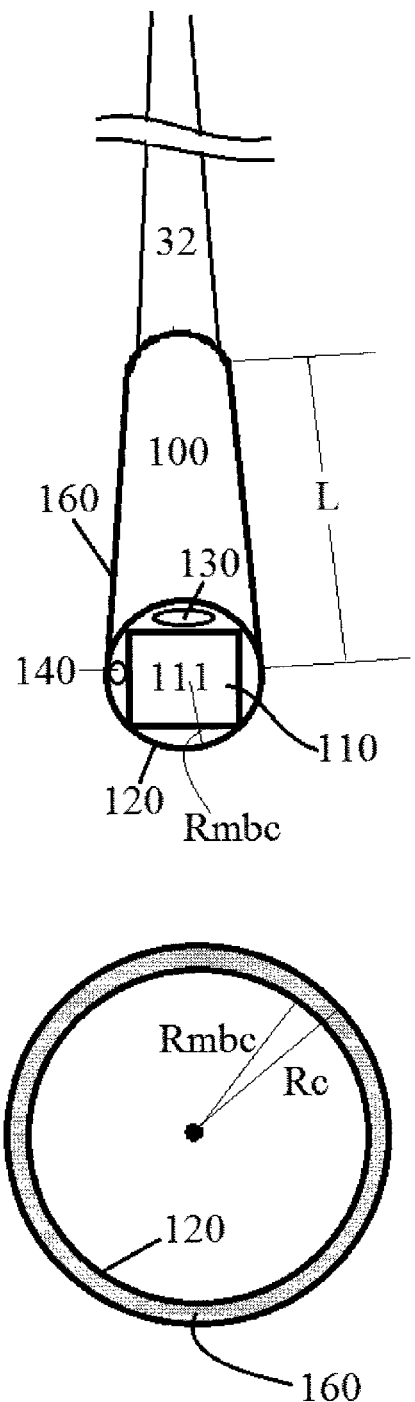
FIG. 3A schematically demonstrates a specific optoelectronic module in accordance with an exemplary embodiment of the present invention.

FIGS. 2A and 3A schematically illustrate the structural configurations of optoelectronic module 100. Referring to FIGS. 2A and 3A, an optoelectronic module 100 comprises a housing 160 and an image sensor 110. The image sensor 110 is located within the housing 160, and it has a face 111 with a perimeter S, which may be in the range of about 2.3 mm to about 6 mm, for example, about 2.3 mm to about 4 mm, and about 4 mm to about 6 mm. The housing 160 may have a thickness of T thinner than 0.1 mm. The cross section of the optoelectronic module along the face 111 has a perimeter H. The perimeter of a circle or ellipse can also be called its circumference. In various embodiments, S<H<1.6S, such as S<H<1.5S, S<H<1.45S, S<H<1.41S, S<H<1.3S, S<H<1.2S, S<H<1.11S, S<H<1.075S, S<H<1.05S, and S<H<1.025S. FIG. 2B shows the cross-sectional view of various optoelectronic module having different designs of the image sensor's face and the housing. A cross sections is the intersection of a body (e.g. optoelectronic module 100) in three-dimensional space with a plane (e.g. face 111). From design (a) to (f), H is decreased from 1.6S to 1.025S, or even down to 1.02S and 1.01S.

Despite the shape and dimension of various parts as illustrated in FIGS. 2A, 2B and 3A, the cross section of optoelectronic module 100 along said face 111 may have any regular shape such as circular, it may have an irregular shape as well. Although face 111 generally has a regular shape such as a polygon, e.g. rectangular and square, it may also have irregular shape.

Referring to FIG. 3A, optoelectronic module 100 comprises an image sensor 110 within a cylinder housing 160. Image sensor 110 has a non-circular face 111. Image sensor 110 is positioned at a distal end (or front tip) of optoelectronic module 100, and non-circular face 111 is pointing forward or facing forward. In various embodiments, image sensor 110 can be any suitable devices having a light sensitive surface (e.g. non-circular face 111) usable for capturing an image, for example, Charged Coupled Device (CCD) and Complementary Metal Oxide Semiconductor (CMOS) image sensors.

Figure 3B:
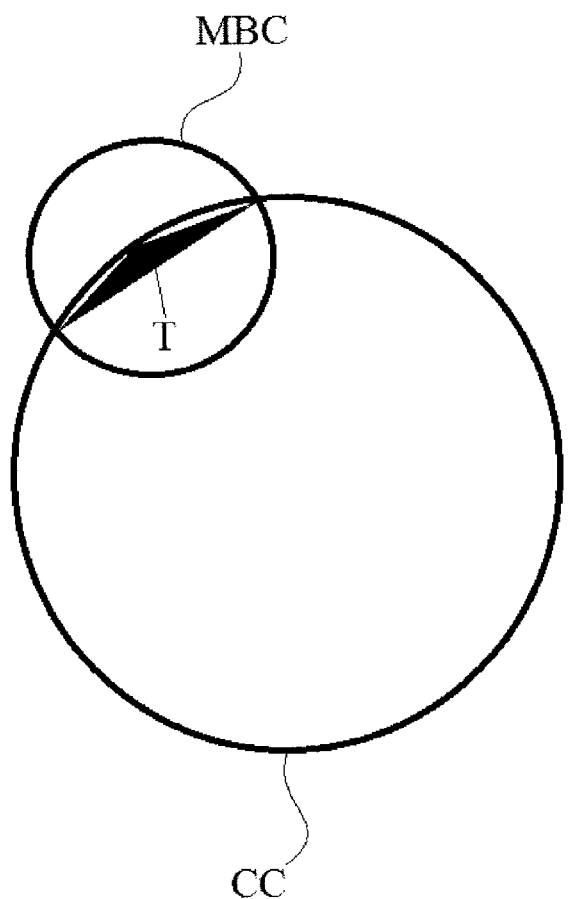
FIG. 3B shows the difference between the circumscribed circle and the minimum bounding circle for the same polygon.

As a principle of plane geometry, a minimum bounding circle 120 may definitely be determined based on any given non-circular planar face 111. It should be appreciated that the concept of "Circumscribed Circle" is different from the concept of "Minimum Bounding Circle" (AKA "Smallest Circle"). Referring to FIG. 3B, in geometry, the circumscribed circle or circumcircle of a polygon (represented as triangle T in FIG. 3B) is a circle denoted as CC which passes through all the vertices of the polygon (3 vertices for triangle T in this example). The center of this circle CC is called the circumcenter and its radius is called the circumradius. A polygon which has a circumscribed circle is called a cyclic polygon (sometimes a concyclic polygon, because the vertices are concyclic). All regular simple polygons, all isosceles trapezoids, all triangles and all rectangles are cyclic.

The smallest-circle problem or minimum covering circle problem is a mathematical problem of computing the smallest circle that contains all of a given set of points in the Euclidean plane. Referring again to FIG. 3B, a minimum bounding circle denoted as MBC is the smallest circle that completely contains the polygon (e.g. triangle T) within it. Not every polygon has a circumscribed circle, as the vertices of a polygon may not all lie on a circle, but every polygon (or even any non-circular irregular 2D shape) has a minimum bounding circle, which may be constructed by a linear time algorithm. As shown in FIG. 3B, even if a polygon has a circumscribed circle, it may not coincide with its minimum bounding circle. For obtuse triangle T, the minimum bounding circle MBC has the longest side as diameter and does not pass through the opposite vertex, and MBC is much smaller than CC.

In various embodiments, the size and dimension of optoelectronic module 100 is designed based on the radius Rmbc of the minimum bounding circle MBC. As shown in FIG. 3A, circular cylinder housing 160 is constructed to have an internal radius which equals to Rmbc, and an external radius Rc. The thickness of housing 160 wall is Th=Rc−Rmbc. Various components of module 100 are confined within a space defined by a right circular cylinder with radius Rmbc and length L, as shown in FIG. 2. There is no special limitation on length L, but L should be kept as short as possible. In some embodiments, length L may be adjusted as desired. For example, when a lens is needed in front of face 111, module 100 can be extended forward a little bit to accommodate the lens, making length L a little bit longer. Alternatively, the lens may protrude from the face 111.

All components of module 100 except the protruded-out lens (if present) are configured to be within housing 160 as defined above. Refereeing to FIGS. 2A, 3A, 4 and 5, these components may include, but are not limited to, one or more illumination components 130, one or more optional working components 140, and an optical component 150, among others.

Although components 130, 140 and 150 can be placed anywhere within the cylinder-shaped housing 160, in preferred embodiments of the invention, illumination components 130 and working components 140 should block face 111 as little as possible, and lens 150 should cover (or overlap with) face 111 as much as possible.

Figure 4:
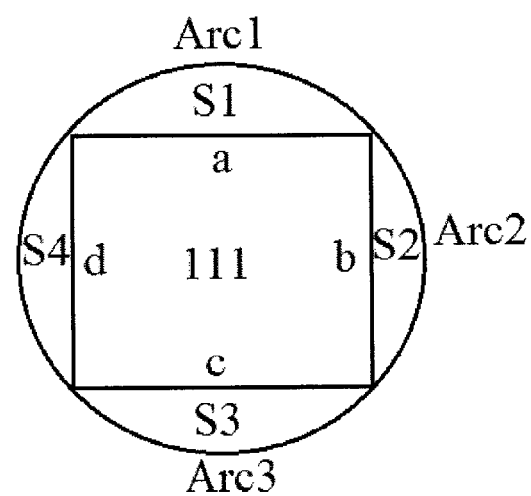
FIG. 4 is a radial cross-sectional view along the non-circular face demonstrating an optoelectronic module in accordance with an exemplary embodiment of the present invention.
Figure 4:
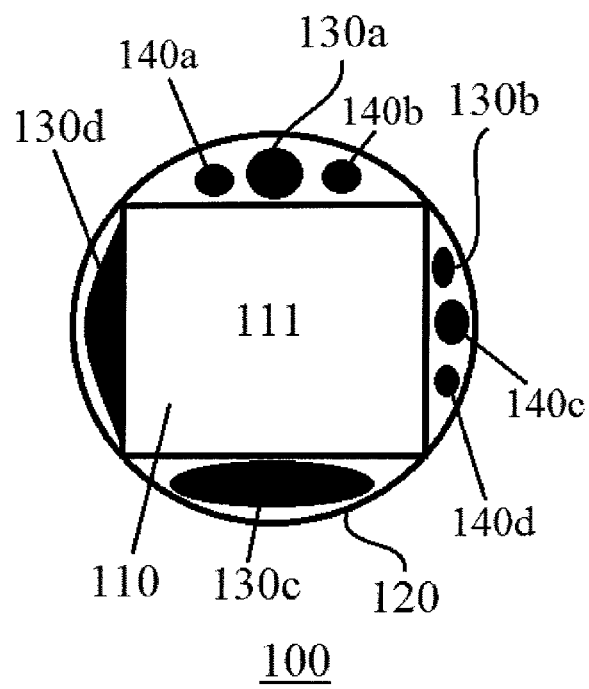

In a representative embodiment, non-circular face 111 has a shape of square, and the diagonal of the square equals to the diameter (2×Rmbc) of the minimum bounding circle 120. However, it should be appreciated that non-circular face 111 may have a shape of any polygon such as triangle, rectangle, pentagon, and hexagon etc. Referring to FIG. 4, a segment can be defined by a chord and an arc. Therefore, four segments (S1, S2, S3, S4) can be defined by 4 sides (a, b, c, d) of square-shaped face 111 as 4 chords, and 4 corresponding arcs (Arc1, Arc 2, Arc3, Arc4) of the minimum bounding circle 120 lying between the 4 chords' endpoints.

As shown in FIG. 4, one or more illumination components 130 (130a, 130b, 130c, 130d) can be arranged in 1, 2, 3, or all of the 4 segments (S1, S2, S3, and S4). By the same token, one or more optional working components 140 (if present) may also be arranged in 1, 2, 3, or all of the four segments (S1, S2, S3, and S4).

Figure 5A:
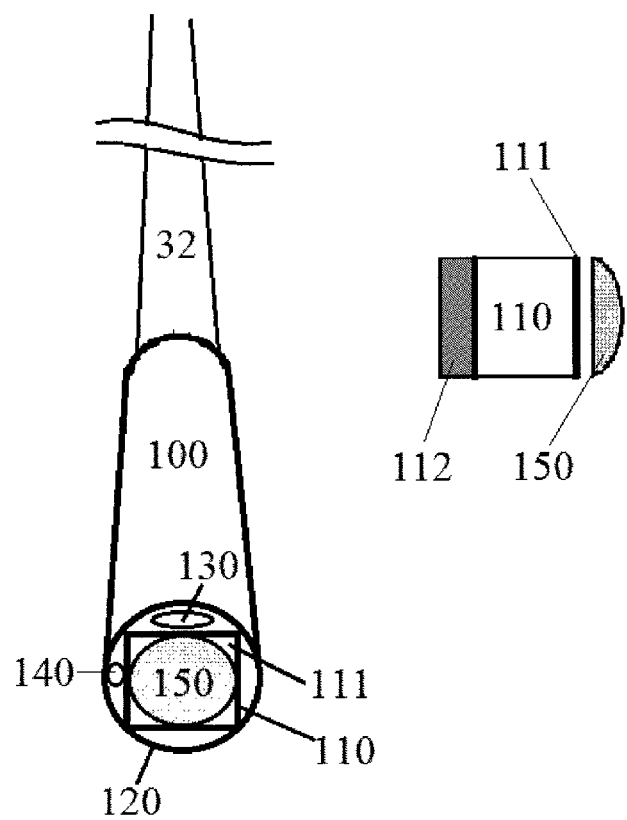
FIG. 5A depicts an optoelectronic module having a lens in accordance with an exemplary embodiment of the present invention.

Referring to FIG. 5A, an electronic circuit board 112, flexible or rigid, may be configured to carry image sensor 110 mounted thereon. Circuit board 112 may supply image sensor 110 with necessary electrical power and may derive still images and/or video feeds captured by the image sensor.

Referring to FIG. 5A, optical component 150 will be described using lens or micro lens 150 as an example. However, it should be appreciated that component 150 may be a catoptric system, or may be a combination of a lens and a catoptric system. Component 150 may include a plurality of optics such as lens assemblies, lenses and protective glass, and is configured to receive reflected light from target objects. A lens assembly may include a plurality of lenses, static or movable, which may provide a field of view of at least 90 degree (90°), typically 120 degree, and up to essentially 180 degree or 230 degree. A lens assembly may provide a depth of field of about 2 to 200 mm.

Figure 5B:
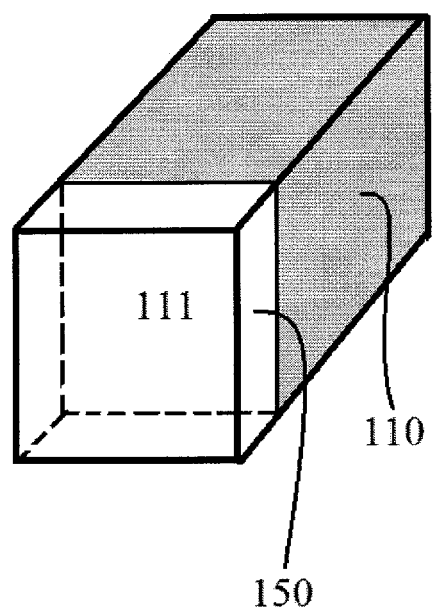
FIG. 5B depicts an optoelectronic module having a square lens that matches a square sensor face in accordance with an exemplary embodiment of the present invention.

In a preferred embodiment as shown in FIG. 5B, lens 150 has the same shape and dimension as face 111. For example, lens 150, exactly like face 111, may be a square lens having a perimeter S. Such a lens and such a sensor face can match (coincide) each other perfectly.

Lens 150 may function as an objective lens, and may comprise coatings such as chromatically correcting coating, and hydrophobic coating. In many applications, a wide-angle objective lens is normally used in order to prevent a situation in which an area of interest such as a lesion area is missed. For example, such objective lens 150 may have an angle of view of 170°-230°. A fish-eye lens having an angle of view of more than 180° may be employed as lens 150. In an operation state, lens 150 focuses the reflected light from the observation target, image sensor 110 detects the focused reflected light, and an A/D converter can convert analog image signals obtained by photoelectric conversion performed by image sensor 110 into digital image signals.

In various embodiments, the lens has a short total optical length (track), for example, 5 mm or less. The lens may be configured to provide a large incident angle, for example, a chief incident angle larger than 20°, such as 20-40°, and provide minimal distortion (for example, less than 80%).

Figure 6:
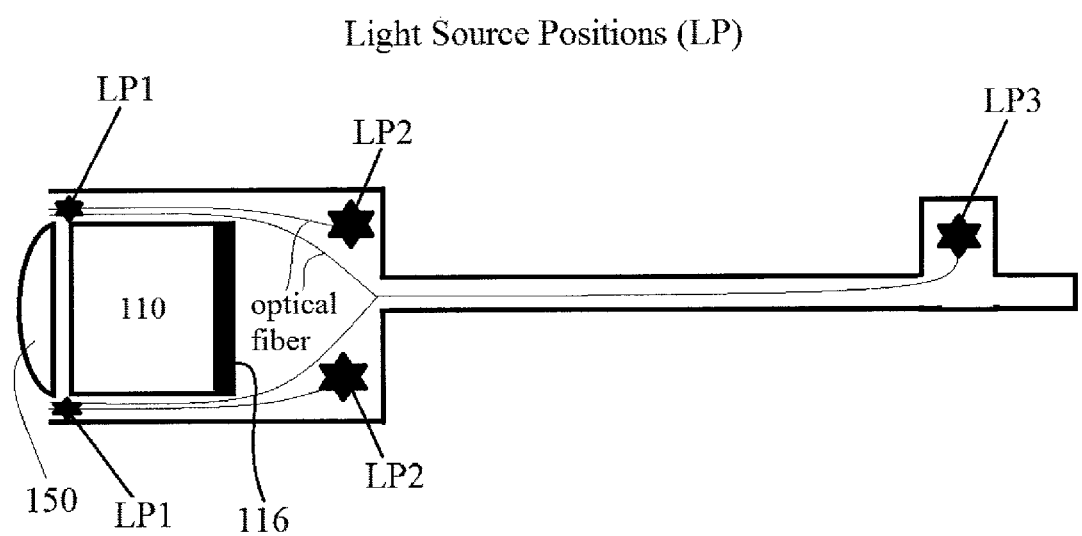
FIG. 6 is an axial cross-sectional view of the optoelectronic module showing different positions of light source in accordance with an exemplary embodiment of the present invention.

Referring to FIGS. 4 and 5A, one or more illumination components 130 can be selected from a light source, an optical fiber optically coupled to a light source, a light diffuser (e.g. an illumination lens) optically coupled to a light source, or any combination thereof. Components 130 independently of each other emit light of same or different wavelength. Examples of light source include a light emitting diode (LED), an incandescent lamp (e.g. halogen lamp), a gas-discharge lamp (e.g. mercury-vapor lamp), a fluorescent lamp, an arc lamp, an ultraviolet lamp such as a Wood's lamp, an infrared lamp, or any combination thereof. Example of LED include a white light LED, an infrared light LED, a near infrared light LED, an ultraviolet light LED or any other LED. Optical fibers are light carriers that carry light from a remotely located light source. Exemplary light diffuser is made of polycarbonate, and is coated with a reflective coating on the surface thereof. Similar to image sensor 110, an electronic circuit board assembly may also be configured to carry LED that is able to illuminate the viewing field of lens 150. In a preferred embodiment, the light source is a flashing LED, which can reduce the "LED ON" time and therefore decrease the heat generated. Flashing LED is particularly useful when module is so small that heat management becomes an important, or even critical. In a more preferred embodiment, such a flashing LED is used with lens 150 and face 111 that have the same shape and dimension (e.g. both are identical square-shaped as shown in FIG. 5B). The flashing LED may be located behind the image sensor 110, and deliveries the light emission to the tip of module 100 through one or more optical fibers 130. As shown in FIG. 6, a light block 116 can be used to prevent any negative impact from, or any interference of, the strong light emission from the LED against the sensor. Light block 116 may be, for example, a coating layer on the back of image sensor 110.

The light source may be located any suitable position in endoscope 30. Referring again to FIG. 6, it may locate at the tip LP1) of optoelectronic module 100. In another embodiment, the light source locates at a middle or rear position (LP2, at the proximal end) within optoelectronic module 100, and deliveries the light emission to the tip of module 100 through one or more optical fibers. In still another embodiment, the light source locates outside optoelectronic module 100 (LP3), and deliveries the light emission to the tip of module 100 through one or more longer optical fibers.

Referring back to FIGS. 4 and 5A, one or more optional working components 140 may be any desired component other than illumination component 130 and optical component such as lens 150. An example of component 140 may be a working channel which may be a hollow opening configured for insertion of a surgical tool to operate on various tissues. For example, miniature forceps may be inserted through working channel in order to remove a polyp or a biopsy sample.

Component 140 may be a channel for injection, inflation, and suction. For example, it can inject fluid (liquid and/or gas) for e.g. cleaning contaminants such as blood, feces and other debris from lens 150. A jet fluid channel may be configured for providing a high pressure jet of fluid, such as water or saline, for cleaning the walls of the body cavity (such as the colon).

In preferred embodiments, a heat management system is incorporated in the optoelectronic module 100. Image sensor, light source such as LED, and related supporting electronic circuitry dissipate some power in the form of heat. Thus, an acceptable optoelectronic module 100 must have an acceptable working temperature and an allowed heat dissipation rate to the patient's body. According to some embodiments of the invention, the use of metal for the construction of an electronic circuit board holder is important for electric conductivity and heat transfer purposes. The electronic circuit board holder can be used as a heat sink for some or all of the electronic components located in module 100 (particularly light source e.g. LEDs) and reduce overall temperature of module 100. This may solve or at least mitigate a major problem of raised temperatures of the endoscope tip and/or any of its components, particularly when using LED illuminators.

A metal support frame may be adapted for use as a heat sink, in accordance with an embodiment of the present specification. To function as a better heat sink, the metal support frame may optionally be equipped with an internal fluid channel. Circulation of fluid within/inside the metal support frame ensures that the distal tip of the endoscope does not overheat and that its temperature is maintained at acceptable levels. In one embodiment, the fluid used within the channels is water. In another embodiment, the fluid is air or gas, such as carbon dioxide.

Figure 7:
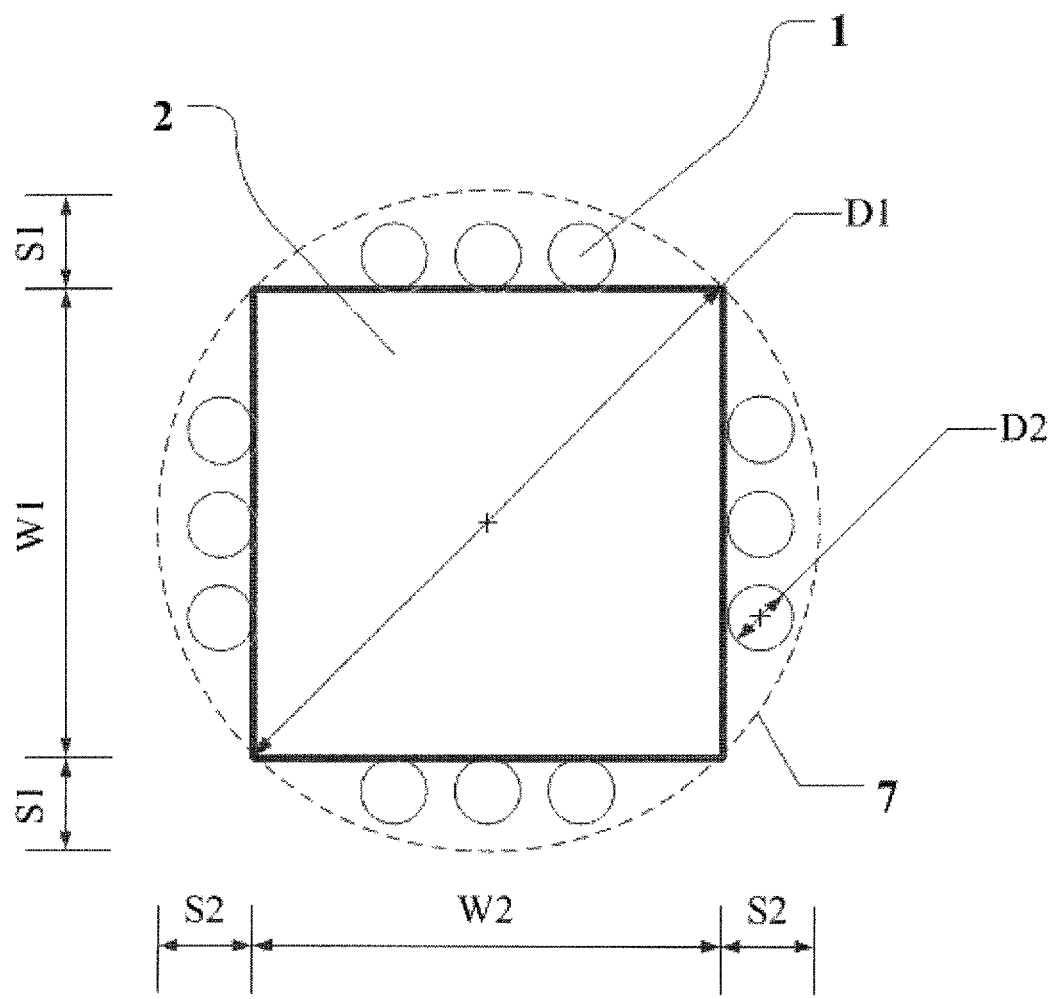
FIG. 7 is a radial cross-sectional view along the non-circular face demonstrating the configuration and dimension of one optoelectronic module in accordance with an exemplary embodiment of the present invention.

FIG. 7 illustrates an exemplary configuration of optoelectronic module 100 of FIG. 4. Circular illumination fibers 1 with a diameter D2 are specific examples of component 130. Rectangular lens 2 is a specific example of optical component 150 as shown in FIG. 5B, with a diagonal length of D1 and side lengths W1 and W2. Image sensor face 111 (not shown) is behind lens 2, and has the same shape as lens 2. Sheath 7 may be a special glued sheath, which is an example of housing 160 as described above. In a specific embodiment as shown in FIG. 7, H is about 1.11S. Three identical fibers 1 are placed in each of the four segments as shown in FIG.

4. For example, a square lens with W1=W2=1.0 mm and D1=1.41 mm is surrounded by twelve fibers 1 with D2=0.17 mm that are evenly distributed in four segments with the same segment height S1=S2=0.21 mm. In other embodiments, each of the four segments may include one big fiber with a diameter 0.17 mm, two medium fibers with a diameter 0.14 mm, and two small fibers with a diameter 0.1 mm.

Figure 8:
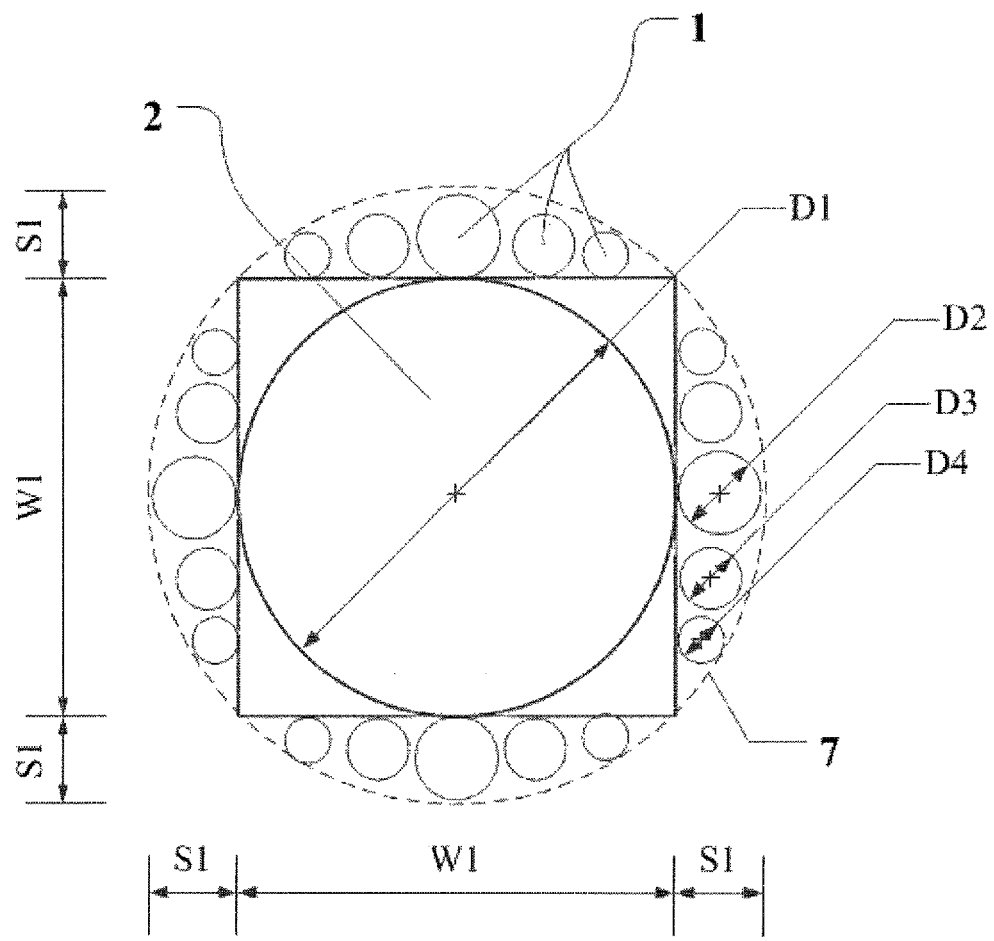
FIG. 8 is a radial cross-sectional view along the non-circular face demonstrating the configuration and dimension of another optoelectronic module in accordance with an exemplary embodiment of the present invention.

FIG. 8 illustrates another exemplary configuration of optoelectronic module 100 of FIG. 4. Circular illumination fibers 1 with different diameters D2, D3 and D4 are specific examples of component 130. Circular lens 2 with a diameter of D1 is a specific example of optical component 150 as shown in FIG. 5B. Square image sensor 110 with a side length W1 is behind lens 2. Sheath 7 may be a special glued sheath, which is an example of housing 160 as described above. In a specific embodiment as shown in FIG. 8, H is about 1.11S. For example, circular lens 2 with a diameter of D1=1.0 mm in front of a square image sensor 110 with side length W1=1.0 mm is surrounded by twenty fibers. In each of the four segments as shown in FIG. 8, there are one big fiber with a diameter D2=0.17 mm, two medium fibers with a diameter 0.14 mm, and two small fibers with a diameter D4=0.1 mm. Each segment height S1 is about 0.20 mm or 0.21 mm. In other embodiments, each of the four segments may include three identical fibers with a diameter of 0.16 mm or 0.17 mm.

Figure 9:
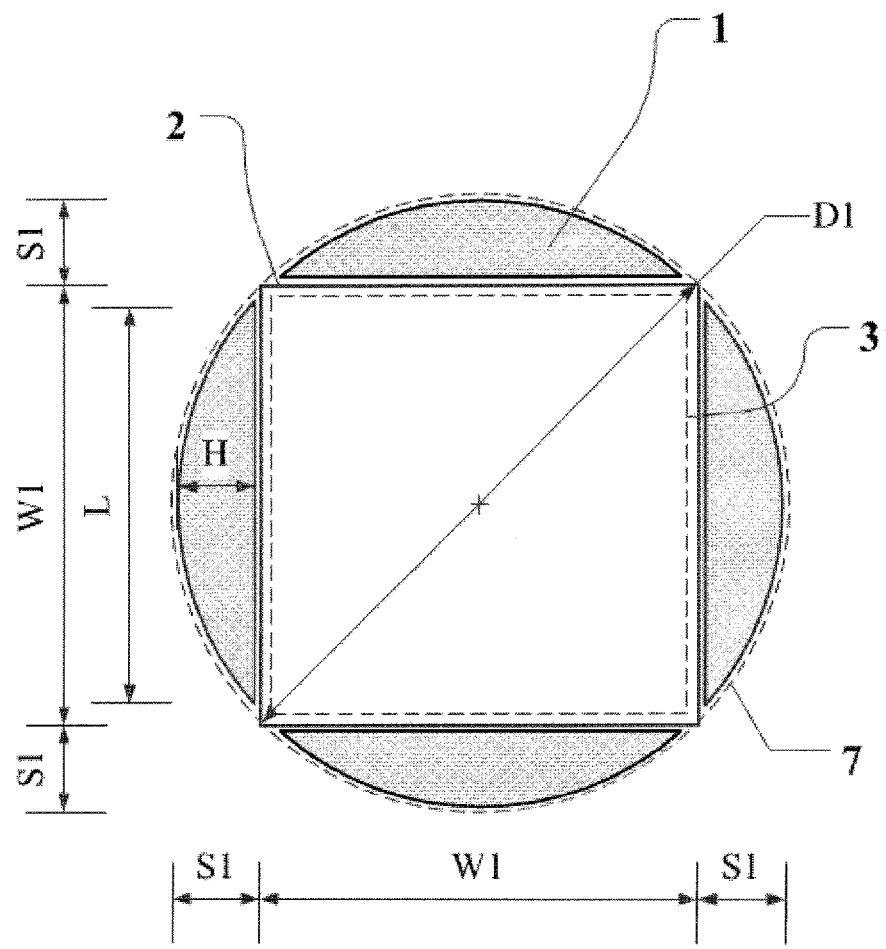
FIG. 9 is a radial cross-sectional view along the non-circular face demonstrating the configuration and dimension of still another optoelectronic module in accordance with an exemplary embodiment of the present invention.

The optical fibers in each segment as described above may be replaced with a single big "D-shaped" fiber. The base length and the height of the D-shaped fiber can be in the ranges of for example 0.7-1.0 mm and 0.16-0.19 mm respectively. FIG. 9 illustrates such a D-shaped fiber. FIG. 9 is substantially the same as FIG. 7, except that the three fibers in each segment are replaced with a single big "D-shaped" fiber with a base length L=0.9 mm and a fiber height H=0.18 mm. Other dimensions in FIG. 9 may be that W1=1.0 mm, S1=0.2 mm, and D1=1.4 mm. Similarly, the five fibers in each segment as shown in FIG. 8 can also be replaced with such a single big "D-shaped" fiber, which will not be repeated here for conciseness.

Figure 10:
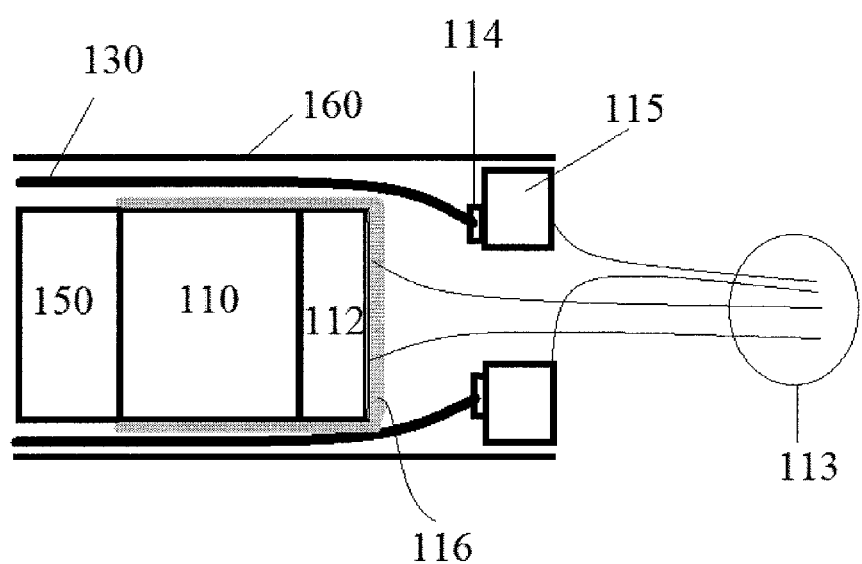
FIG. 10 is a radial cross-sectional view demonstrating the configuration of an optoelectronic module in accordance with an exemplary embodiment of the present invention.

FIG. 10 is an axial cross-sectional view of an exemplary configuration of optoelectronic module 100. Within housing 160, a microlens system 150 (e.g. a square lens) is placed in front of CMOS sensor 110, which is mounted on a circuit board 112. Light block 116 is placed behind circuit board 112 and around CMOS sensor 110 so that face 111 will detect only the reflected light form the observed object, and will not be disturbed by the strong light from LED 114. LED 114 is mounted on circuit board 115, and the light emitted from LED 114 is delivered to the tip of module through optical guide 130 (e.g. optical fibers as shown in FIGS. 7, 8 and 9). Electrical wires 113 are connected to circuit boards 112 and 115.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. An optoelectronic module comprising a housing, an image sensor, and one or more optical fibers optically coupled to a light source,
   wherein the image sensor is located within the housing,
   wherein the image sensor's face has a perimeter S,
   wherein the cross section of the optoelectronic module along said face has a perimeter H, and S<H<1.6S,
   wherein the light source is located at rear position or the proximal end within said optoelectronic module, and uses an electronic circuit board holder in the module as a heat sink,
   wherein said one or more optical fibers deliver light emitted from the light source to the tip of said optoelectronic module,
   wherein the image sensor comprises a CMOS sensor, and
   wherein said one or more optical fibers comprise a D-shaped fiber with a base length and a height in the ranges of 0.7-1.0 mm and 0.16-0.19 mm respectively.

2. The optoelectronic module according to claim 1, wherein the housing is cylinder-shaped, and the image sensor has a non-circular face,
   wherein the internal diameter of the cylinder-shaped housing is the same as the diameter of a minimum bounding circle of said non-circular face, and
   wherein said image sensor and said one or more optical fibers are confined within the cylinder-shaped housing.

3. The optoelectronic module according to claim 2, wherein the non-circular face has a shape of square, and the diagonal of the square equals to the diameter of the minimum bounding circle.

4. The optoelectronic module according to claim 3, wherein four segments are defined by four sides of said square as four chords and four corresponding arcs of said minimum bounding circle lying between said four chords' endpoints, rand wherein at least one of the four segments comprises said one or more optical fibers.

5. The optoelectronic module according to claim 4, wherein at least one of the four segments comprises a working channel for insertion of a surgical tool, injection, inflation, and, suction.

6. The optoelectronic module according to claim 2, further comprising a lens in front of the non-circular face.

7. The optoelectronic module according to claim 6, wherein both the lens and the face have identical shape and dimension, and are configured to coincide each other.

8. The optoelectronic module according to claim 1 wherein the CMOS sensor comprises an array of at least 400×400 pixels.

9. The optoelectronic module according to claim 1, wherein said one or more optical fibers independently of each other emit light of same or different wavelength.

10. The optoelectronic module according to claim 1, wherein said light source comprises a light emitting diode (LED), an incandescent lamp, a gas-discharge lamp, a fluorescent lamp, an arc lamp, an ultraviolet lamp such as a Wood's lamp, an infrared lamp, or any combination thereof.

11. The optoelectronic module according to claim 10, wherein said light source is a flashing LED.

12. An imaging apparatus for imaging the interior surface of a tubular structure, comprising
   (1) optoelectronic module according to claim 1 for insertion into the tubular structure;
   (2) a receiving device outside the tubular structure for receiving the signal from the image sensor; and
   (3) a cable having (i) a distal end connected to the proximal end of the optoelectronic module, and (ii) a proximal end connected to the receiving device.

13. The imaging apparatus according to claim 12, which is an industrial endoscope.

14. The imaging apparatus according to claim 12, wherein said interior surface of a tubular structure is an inner surface of a lumen in a body, and the imaging apparatus is an endoscope for human medicine and veterinary medicine.

15. The imaging apparatus according to claim 12, wherein the cable is configured to extend proximately through the tubular structure to enable a force to be applied to the optoelectronic module to control the movement thereof within the tubular structure, and to permit retraction of the optoelectronic module from the tubular structure.

16. The imaging apparatus according to claim 12, wherein the cable includes at least one electrical lead that is coupled to the optoelectronic module and conveys an electrical signal from the optoelectronic module to the receiving device.

17. The imaging apparatus according to claim 12, wherein the cable includes a plurality of scale markings that serve to enable a user to measure a distance traveled by the optoelectronic module within the tubular structure.

18. The imaging apparatus according to claim 12, further comprising a processor programmed with software that accepts as input a plurality of still images of an object generated by the optoelectronic module and outputs for display a three-dimensional rendering of the object based on the plurality of still images.

\* \* \* \* \*